(12) United States Patent
Faber et al.

(10) Patent No.: US 6,242,263 B1
(45) Date of Patent: *Jun. 5, 2001

(54) AUTOMOTIVE HYDROCARBON SENSOR

(75) Inventors: Margaret K. Faber, Corning; Yuming Xie, Painted Post; Zhigang Zhou, Corning, all of NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/203,085

(22) Filed: Dec. 1, 1998

Related U.S. Application Data (63) Continuation-in-part of application No. 08/980,295, filed on Nov. 28, 1997, now abandoned
(60) Provisional application No. 60/033,139, filed on Dec. 20, 1996, and provisional application No. 60/033,141, filed on Dec. 20, 1996.

(51) Int. Cl.[7] .................................................. F01N 3/10
(52) U.S. Cl. .......................... 436/143; 436/137; 422/94; 422/98; 73/23.32
(58) Field of Search .......................... 422/94, 95, 98; 436/143, 147, 137, 142; 73/23.32; 204/424, 426

(56) References Cited

U.S. PATENT DOCUMENTS

| | | |
|---|---|---|
| 2,980,743 | 4/1961 | Toft . |
| 3,898,181 | 8/1975 | Barker . |
| 3,906,721 | 9/1975 | Micheli et al. . |
| 3,914,376 | 10/1975 | Barker . |
| 4,006,103 | 2/1977 | Meguerian et al. . |
| 4,012,485 | 3/1977 | Meguerian et al. . |
| 4,036,592 | 7/1977 | Brown et al. . |
| 4,128,506 | 12/1978 | Hegedus et al. . |
| 4,171,287 | 10/1979 | Keith . |
| 4,289,737 | 9/1981 | Acres et al. . |
| 4,624,940 | 11/1986 | Wan et al. . |
| 4,975,406 | 12/1990 | Frestad et al. . |
| 4,976,929 | 12/1990 | Cornelison et al. . |
| 5,157,204 | 10/1992 | Brown et al. . |
| 5,177,464 | 1/1993 | Hamburg . |

(List continued on next page.)

FOREIGN PATENT DOCUMENTS

| | | |
|---|---|---|
| 0 751 390 | 1/1997 | (EP) . |
| 59-0058116 | 4/1984 | (JP) . |

*Primary Examiner*—Lyle A. Alexander
(74) *Attorney, Agent, or Firm*—Timothy M. Schaeberle (57) ABSTRACT

A system for measuring the non-methane HC concentration of gas sample, e.g., automotive exhaust gas, comprises a sensor catalyst capable of selectively oxidizing the combination of $CO+H_2+$alkene hydrocarbons in a gas sample and a catalytic differential calorimetric sensor downstream of the sensor catalyst, capable of producing an output signal representative of the exothermic effect of oxidation of the remaining aromatic and alkane hydrocarbons in the gas sample. The system also includes a heater for maintaining both the sensor catalyst and the catalytic calorimetric sensor at a temperature sufficient to achieve substantially complete oxidation of the $CO+H_2+$alkene hydrocarbon combination and the aromatic and alkane hydrocarbons, respectively. Lastly, the system includes a means for analyzing the output signal representative of the concentration of unburned aromatic and alkane hydrocarbons in the exhaust gas to determine concentration of the total non-methane hydrocarbon species. A method carried out by the system comprises the following steps: (1) contacting a portion of a exhaust gas sample with a sensor catalyst which selectively oxidizes a combination of $CO+H_2+$alkene hydrocarbons; and thereafter, (2) contacting the oxidized portion of the exhaust gas sample with a sensor producing an output signal representative of the concentration of the remaining aromatic and alkane hydrocarbons in the oxidized exhaust gas portion; (3) analyzing the output signal thereby determining the total hydrocarbon concentration in the exhaust gas.

12 Claims, 9 Drawing Sheets

U.S. PATENT DOCUMENTS

| | | |
|---|---|---|
| 5,255,511 | 10/1993 | Maus et al. . |
| 5,265,417 | 11/1993 | Visser et al. . |
| 5,314,828 | 5/1994 | Dalla Betta et al. . |
| 5,408,215 | 4/1995 | Hamburg . |
| 5,444,974 | 8/1995 | Beck et al. . |
| 5,472,580 | 12/1995 | Kennard, III et al. . |
| 5,476,001 | 12/1995 | Hoetzel et al. . |
| 5,486,336 | 1/1996 | Dalla Betta et al. . |
| 5,494,701 | 2/1996 | Clough et al. . |
| 5,494,826 | 2/1996 | Stetter et al. . |
| 5,517,848 | 5/1996 | Hosoya et al. . |
| 5,560,200 | 10/1996 | Maus et al. . |
| 5,597,772 | 1/1997 | McCabe et al. . |
| 5,687,565 | 11/1997 | Modica et al. . |
| 5,689,059 | 11/1997 | Oh et al. . |
| 5,795,545 | 8/1998 | Koripella et al. . |
| 5,798,270 | 8/1998 | Adamczyk et al. . |
| 5,858,306 | 1/1999 | Oh et al. . |
| 5,922,287 * | 7/1999 | Kato et al. ............... 422/95 |
| 6,037,183 * | 3/2000 | Faber et al. ............ 436/137 |

* cited by examiner

AUTOMOTIVE HYDROCARBON SENSOR

This application is a continuation-in-part of application Ser. No. 08/980,295, filed Nov. 28, 1997, now abandoned which claims the benefit of U.S. Provisional Application No. 60/033,139, filed Dec. 20, 1996, entitled "AUTOMOTIVE HYDROCARBON SENSOR" by Margaret K. Faber and Yuming xie, and Ser. No. 60/033,141, filed Dec. 20, 1996, entitled RHODIUM CATALYST FOR PURIFYING EXHAUST GASES, by Yuming Xie.

BACKGROUND OF THE INVENTION

1. Field of the Invention

The present invention relates generally to the technology of measuring the non- methane hydrocarbon concentration in the emissions of an automotive internal combustion engine, and more particularly to the use of a selective catalyst and a catalytic differential calorimetric sensor to monitor the non-methane hydrocarbon oxidation efficiency of an exhaust system's catalytic converter.

2. Description of the Related Art

Catalytic converters have been used on gasoline-fueled automobiles produced in the United States since the mid-1970's for the purpose of promoting the oxidation of unburned hydrocarbons (HCs) and of carbon monoxide (CO). Soon after their introduction, the converters were adapted to promote the chemical reduction of oxides of nitrogen ($NO_x$). At the present time these converters typically employ small amounts of platinum, palladium and rhodium dispersed over a high surface area particulate carrier vehicle which, in turn, is distributed as a thin, porous coating (sometimes called a washcoat) on the wall of a ceramic monolith substrate. The substrate is typically formed by an extrusion process providing hundreds of thin wall, longitudinal parallel open cells per square inch of cross section. These flow-through catalytic devices are housed in a suitable stainless steel container and placed in the exhaust stream under the vehicle downstream from the engine's exhaust manifold.

Under warm, steady-state engine conditions, this conventional catalytic converter containing the precious metal based three-way catalyst (TWC), so called because it simultaneously achieves the oxidation of CO and unburned HCs and the reduction of $NO_x$, effectively and efficiently converts most of the HC, CO and NOx from automotive emissions. However, the catalyst system may become malfunctioning after experiencing thermal aging at an unusually high temperature due to high exposure to poisoning gases like $SO_2$, Pb, and Si, etc. Furthermore, new emissions regulations require an extended durability of the catalytic converter from 50,000 miles to 100,000 miles. Lastly, as a means to ensure that vehicles meet the certified emission standards throughout the vehicle's operation life, On-Board Diagnostics-II (OBD-II) regulation, as passed by the California Air Resource Board (CARB), calls for continuous monitoring of the hydrocarbon conversion efficiency of catalytic converters by direct measurement of the hydrocarbon emission in the exhaust system after the catalyst light-off Specifically, the monitoring system should be able to indicate when the catalyst system is malfunctioning and its conversion capability has decreased to the point where either of the following occurs: (1) HC emissions exceed the applicable emission threshold of 1.5 times the applicable Federal Test Procedure (FTP) HC standard for the vehicle; and (2) the average FTP Non-methane Hydrocarbon (NMHC) conversion efficiency of the monitored portion of the catalyst system falls below 50 percent.

On the other hand, automotive emissions before the catalyst system's catalytic converter has warmed up to operational temperatures, namely, cold start emissions, contribute the majority of pollution from automobiles. Approaches such as, catalytic converters, close coupled to the engine, which heat and begin to function within a few seconds, electrically heated catalytic converters and in-line adsorbers which temporarily store unburned hydrocarbons until the catalytic converter lights off, have all been proven to be effective solutions for the reduction of cold start emissions. Again, OBD-II regulations require that systems be installed in the exhaust system to directly monitor the functional status of any of these "cold-start" devices during the lifetime of the car (100,000 miles).

The use of hydrocarbon sensors as on-board catalytic efficiency monitors is a relatively new technological area that has generated increasing interest for the auto industry as a result of OBD-II legislation. Generally, the use of a catalytic calorimetric sensor, which measures the effect of the exotherm of the catalyzed oxidation of the hydrocarbons over supported precious metal catalysts on the resistance of a coil conductor is known.

U.S. Pat. No. 5,408,215 (Hamburg et al.) generally discloses a system comprising: (1) a test chamber remote from the engine exhaust gas stream; (2) means for alternately supplying the chamber with an upstream and a downstream exhaust gas stream sample; (3) a hydrocarbon sensor exposed to the exhaust gas samples in the chamber to produce a signal responsive to the concentration of hydrocarbon in the chamber; and, (4) a means for comparing the downstream and upstream signals to produce a sensed signal for comparison with a reference signal to determine if the converter is faulty.

U.S. Pat. No. 5,265,417 (Visser et al.) discloses a method comprising the steps of (1) determining the hydrocarbon concentration of the exhaust gas upstream and downstream of the converter by alternately sampling the upstream and downstream exhaust gas and passing the samples to a catalytic differential calorimetric sensor; (2) comparing the hydrocarbon content of the upstream and downstream exhaust gas samples and thereby determining the hydrocarbon conversion efficiency of the catalytic converter.

A shortcoming common to both Visser and Hamburg is the necessary measurement of both an upstream and downstream exhaust gas sample at a position remote from the exhaust gas stream. This is accomplished through the use of combination of a remote sensing chamber and a valving and delivering system that is capable of delivering alternate samples of the upstream and downstream exhaust. As a result of the complexity of these systems exhibit an increased possibility of system failure during the lifetime of the vehicle; e.g., dirty and/or rusty valving may decrease the accuracy of the HC measurement.

Lastly, U.S. Pat. No. 5,444,974 (Beck et al.) discloses a method diagnosing the performance of the catalytic converter for the oxidation of CO and HC involving producing an electrical signal from a calorimetric sensor located in the exhaust stream downstream of the catalytic converter. The calorimetric sensor is comprised of a first portion bearing an oxidized catalyst for CO, $H_2$ and HC and an adjacent second portion that is oxidation catalyst-free.

Common to all three of these systems is the disclosure of a non-selective or "total" sensor which not only measures the HC species but also the CO and $H_2$ species present in the exhaust gas. All three references teach the use of a calorimetric sensor, while Hamburg and Visser additionally disclose the use of a semiconductor-type with a material that adsorbs gases; none of the references provide any teaching as to how to make the sensors selective for HCs alone. Given the fact that a properly functioning catalytic converter, after light-off, typically produces an exhaust gas hydrocarbon concentration, which is typically on the order of tens (or below) ppm, while the CO concentration is typically an order of magnitude greater, none of these diagnostic systems are capable of directly and selectively measuring HC concentration in this concentration range. Specifically, these sensor systems do not compensate or account for these interfering gases, especially the CO, which are present in concentrations far greater than the HC species. As such, the systems exhibit a reduced ability to accurately measure the HC concentration.

SUMMARY OF THE INVENTION

Accordingly, the present invention, in its broadest sense, is directed at a system and a method for selectively and directly measuring the non-methane hydrocarbon concentration in a gas sample; e.g., the exhaust gases produced by an internal combustion engine. In either the system or the method, a hydrocarbon sensor is used which is capable of detecting, under a variety of engine and fuel conditions, including cold start conditions, low (ppm) concentrations of non-methane hydrocarbons in exhaust gases, containing a variety of gaseous components. The location of the system, or performance of the method, at a location downstream of a catalytic converter, results in a configuration that has particular utility in catalytic converter efficiency monitoring.

Simply stated, the system comprises a sensor catalyst capable of selectively oxidizing the combination of $CO+H_2+$ alkene hydrocarbons in a gas sample and a catalytic differential calorimetric sensor downstream of the sensor catalyst, capable of producing an output signal representative of the exothermic effect of oxidation of the remaining aromatic and alkane hydrocarbons in the gas sample. Also provided in the system is a heater for maintaining both the sensor catalyst and the catalytic calorimetric sensor at a temperature sufficient to achieve substantially complete oxidation of the $CO+H_2+$alkene hydrocarbon combination and the aromatic and alkane hydrocarbons, respectively. Lastly, the system includes a means for analyzing the output signal representative of the concentration of unburned aromatic and alkane hydrocarbons in the exhaust gas to determine concentration of the total non-methane hydrocarbon species.

In one embodiment, the system, incorporated within tubular housing located an internal combustion engine's exhaust system, includes a sensor catalyst having an oxidation catalyst which selectively oxidizes the $CO+H_2+$alkene hydrocarbons in the exhaust gas sample. Furthermore, catalytic differential calorimetric sensor comprises a substrate having a first catalytic portion having an oxidation catalyst capable of oxidizing the remaining oxidizable species of the exhaust gas sample, aromatic and alkane hydrocarbons, and an adjacent second reference portion.

In its simplest form the method of measuring the hydrocarbon concentration comprising the steps of: (1) contacting a portion of a exhaust gas sample with a sensor catalyst which selectively oxidizes a combination of $CO+H_2+$alkene hydrocarbons; and thereafter, (2) contacting the remaining un-oxidized portion of the exhaust gas sample with a sensor producing an output signal representative of the concentration of the aromatic and alkane hydrocarbons remaining in the exhaust gas sample; (3) analyzing the output signal thereby determining the total hydrocarbon concentration in the exhaust gas.

DETAILED DESCRIPTION OF THE INVENTION

Apparatus

The present invention is directed at a system for measuring the hydrocarbon concentration of a gas sample. In its simplest embodiment, the system comprises a selective sensor catalyst and a downstream catalytic differential calorimetric sensor, the sensor capable generating an output signal representative of the oxidation exothermic effect it is subject to. The sensor catalyst located upstream of the sensor is capable of selectively oxidizing the combination of $CO+H_2+$alkene hydrocarbons in the gas sample while the sensor's signal is representative of the oxidation of the remaining oxidizable species in the gas sample; i.e., the alkane and aromatic hydrocarbons. The system also includes a heater for maintaining the sensor catalyst and the sensor at a sufficient temperature to ensure the respective oxidations each is subject to. Lastly, the system includes a means for analyzing the output signal to indicate the concentration of unburned aromatic and alkane hydrocarbons remaining in the gas sample; which directly correlates to the total non-methane hydrocarbon concentration.

Figure 1:
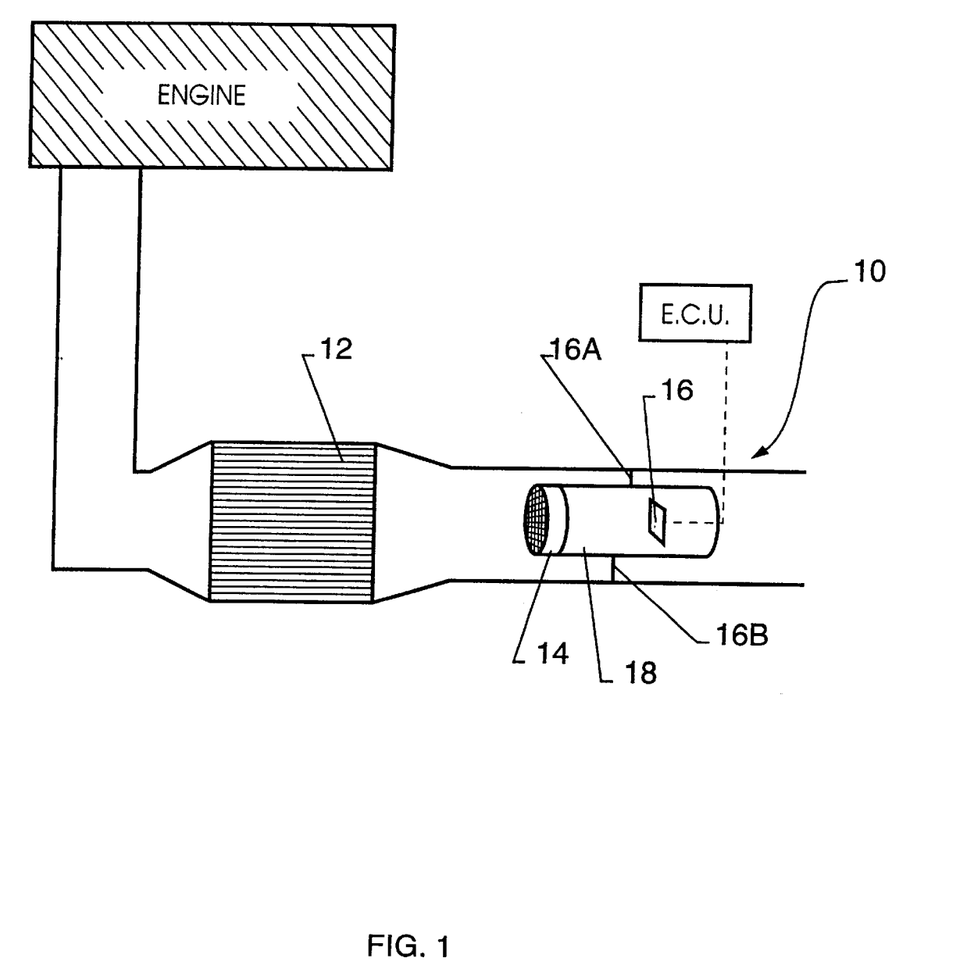
FIG. 1 is a schematic diagram of an embodiment of inventive system for measuring hydrocarbon concentration of an exhaust gas stream.

Referring to FIG. 1, illustrated therein is a schematic representation of the system 10 for measuring hydrocarbon concentration of exhaust gases in an exhaust stream, according to one embodiment of the present invention. A main catalytic converter 12 is located in the exhaust gas downstream of an internal combustion engine. This main catalytic converter 12 is capable of catalyzing the exhaust gas so as to reduce the pollutants present in the exhaust gas. Preferably, the catalyst is a three-way catalyst which functions to oxidize HCs, CO, $H_2$, as well as to reduce $NO_x$, in the exhaust gas. The monitoring system 10 generally comprises a sensor catalyst 14 and a catalytic differential calorimetric sensor 16 to directly measure the non-methane hydrocarbon concentration in the exhaust gas. Hydrocarbons as oxidized/measured and referred to herein, refer to non-methane hydrocarbons (HC).

Referring still to FIG. 1 the hydrocarbon measurement system 10 includes a housing 18, located downstream of the catalytic converter 12, within which are disposed both the selective sensor catalyst 14 and the catalytic differential calorimetric sensor 16; supports 16A and 16B are used to support the sensor 16. On the other hand, to measure the concentration of an upstream portion of exhaust gas, the housing, sensor catalyst and the sensor could be located upstream of the main converter.

In one embodiment, the sensor catalyst comprises a honeycomb substrate oxidation catalyst having coated thereon a catalyst-support material, and upon which an appropriate "selective" catalytically active precious metal is deposited. Suitable catalytic-support materials include any high surface area material, preferably a ceramic material, including for example, silica, alumina, zirconia, ceria, titania and mixtures thereof.

Although a honeycomb body is the preferred form of substrate upon which the catalyst-support material is placed, the substrate can comprise any number of forms. For example, the substrate upon which is coated the catalyst-support material can be in the form of other geometrical or particle forms such as spheres, rings, hollow cylinders, granules (beads or pellets) or other shapes Additionally, the substrate itself simply be comprised of the catalyst-support material.

As indicated above it is essential that the oxidation catalyst includes a catalytically active precious metal which selectively oxidizes the $CO+H_2$+alkene HC combination. One such oxidation catalyst comprises an amount of highly dispersed Rh-cluster deposits on a high surface area catalyst-support material, preferably silica. The oxidation catalyst according to the invention should be prepared in accordance with a method that ensures that the Rh-cluster deposits on the high surface area catalyst-support material are highly dispersed. Specifically, "highly-dispersed" as used herein, refers to Rh-cluster deposits covering no greater than about 10% of the surface area of the support material, preferably no greater than about 5% of the surface area of the support material. Furthermore, the method of catalyst preparation should ensure that the Rh-cluster deposits exhibit the proper size, as deposited on the surface catalyst-support material. The Rh-cluster deposits, comprised of a single rhodium atom or a cluster of at least two Rh atoms, should exhibit a diameter of less than about 5 nm, preferably less than about 1 nm, most preferably less than about 5 Å. If the Rh-deposits are too closely spaced together they will effectively function as if a precious metal layer is deposited on the support material surface, the result being a loss of the selective oxidation feature which is obtained as a result of the small size and high dispersion of the Rh-deposits.

In addition to the aforementioned limitation on the surface area coverage of the Rh-cluster deposits, which exhibit a hemispherical-like shape on the catalyst support surface, it is critical that the total amount of rhodium comprise an amount on the catalytic-support material, which will be sufficient to provide a small but catalytically effective amount of the rhodium metal to substantially and completely catalyze the $CO+H_2$+alkene HCs in an exhaust gas portion. For example, the total amount of Rh that should be deposited on a catalyst-support having an approximate area of 150 $m^2/g$, should be less than about 0.3%, by weight, of the total oxidation catalyst weight, and preferably, less than about 0.1%, by weight of the total oxidation catalyst. This small amount of Rh loading ensures that the Rh clusters remain highly dispersed and thus the Rh-containing catalyst remains highly selective.

In these catalysts the precious metal rhodium component is the main catalytically active component in the catalytic reaction, and it is the principal aim of the highly dispersed and small sized rhodium to contribute to ability of oxidation catalyst to selectively oxidize the $CO+H_2$+alkene HC species. While not intending to be limited by the theory it is thought that the selective nature of the inventive rhodium-containing oxidation catalyst is based on a combination of the highly dispersed nature and small size of the rhodium cluster deposits which are deposited on the surface of the catalytic- support material.

The "catalyst-support material", a powdered material with a high specific surface area, upon which the precious metal rhodium is applied provides support for the highly-dispersed Rh-metal clusters. Suitable catalyst-support materials, described briefly above, include materials selected from the group consisting of silica, alumina, titania, zirconia, zeolite materials as well as mixtures thereof For the following reasons, a preferable catalyst-support material comprises silica: (1) silica ($SiO_2$) is more acidic and thus exhibits a reduced affinity, when compared to alumina, titania and zirconia, for attracting the $SO_2$ molecule, therefore reducing $SO_2$ concentration over the $SiO_2$ surface which directly results in less contact of $SO_2$ with the active Rh site (poisoning); (2) silica exhibits a greater static reaction effect, thus resulting in a greater ability to hold the Rh-cluster deposits in highly dispersed states. Alumina is suitable for use as the catalytic support material, however, it has stronger interaction with $SO_2$ thus $SO_2$ has a more profound poisoning effect on the catalytic activity when compared to $SiO_2$ at a given temperature. As such, an alumina supported Rh-catalyst would require a higher operating temperature thus resulting in a smaller "window" for oxidation to occur before the HCs begin to self ignite; as compared to a catalytic "window" for the preferred catalytic-support material, silica.

A suitable procedure for preparing the Rh-containing catalyst, so as to ensure high dispersion, small sized Rh-cluster deposits on the surface of the catalytic-support material, in accord with the present invention generally involves the following steps: (1) adding a Rh-containing compound (e.g., rhodium chloride) to a solvent (e.g., $H_2O$) to form a Rh-containing solution and thereafter adding an adequate amount of an ammonium-containing solution (e.g. NH4OH) to form an Rh-ammonium solution; (2) impregnating an amount of a high surface area catalyst-support material powder with the Rh-ammonium solution by incipient wetness impregnation and thereafter drying and calcining this impregnated powder to form a dry powder mixture comprised of the high surface area catalytic-support material with highly dispersed Rh-deposits located on the surface.

A variety of Rh-containing compounds may be used in the above procedure including the nitrates, halides, acetonulacetonates or appropriate rhodium carbonyls; in other words any rhodium-containing material can be used as long as the result is small sized, highly dispersed Rh-cluster deposits.

Figure 2:
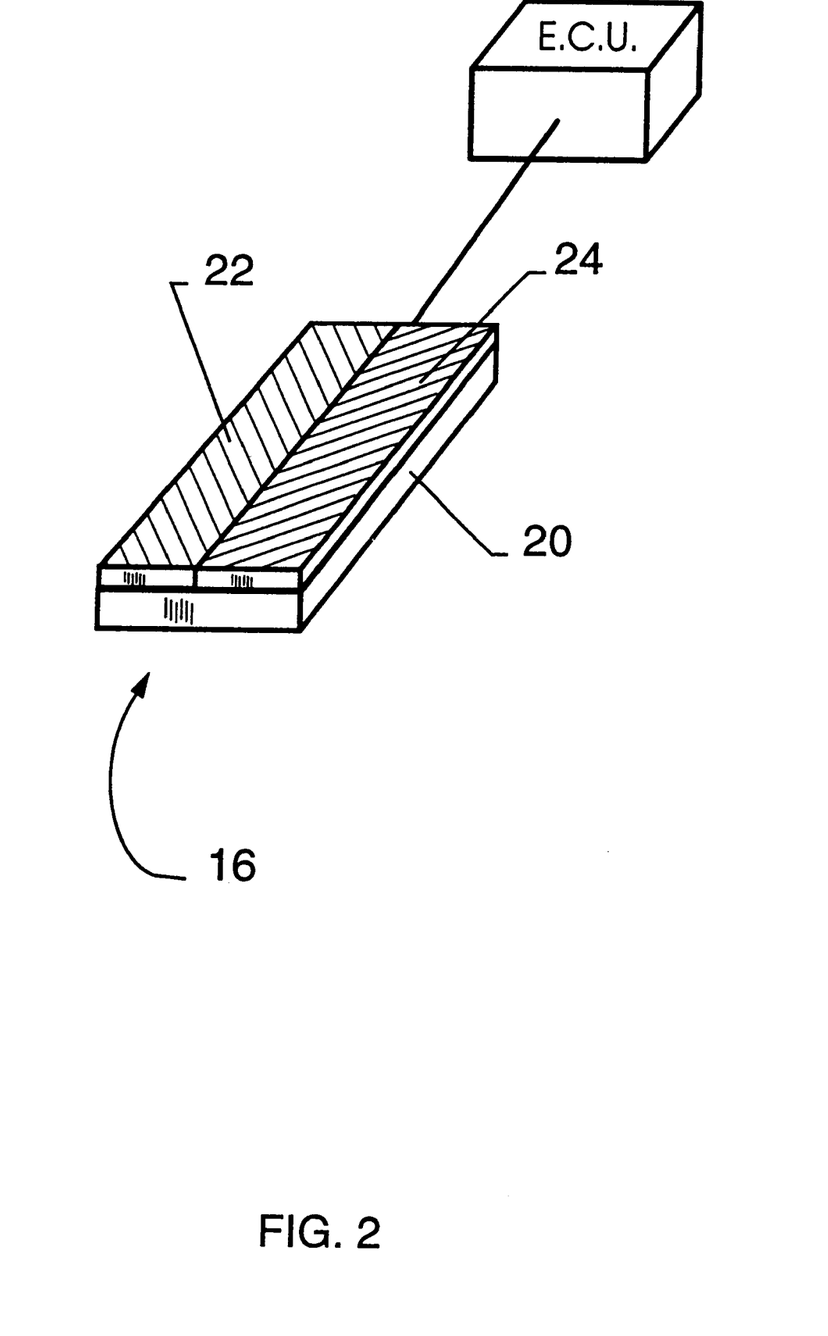
FIG. 2 is a schematic diagram of the catalytic differential calorimetric hydrocarbon sensor described herein.

Referring now to FIG. 2 illustrated therein is a schematic perspective view of the sensor that is utilized in the instant invention. Catalytic differential calorimetric sensor 16, is a divided sensor device, a portion of which is catalytically active. Sensor 16 is comprised of a substrate 20 comprising a first portion 22 having deposited thereon a second oxidation catalyst comprising a catalyst-support material and a catalytically active precious metal capable of oxidizing the remaining oxidizable species in a downstream portion of the exhaust gas already oxidized by the sensor catalyst 14. Sensor 16 further comprises an adjacent second reference portion 24 having deposited thereon an uncatalyzed support material. Oxidation of the remaining oxidizable species (alkane and aromatic HC), an exothermic reaction in which energy is released, will raise the temperature of the first catalytic portion 22 above that of the non-catalyzed second reference portion 24.

Sensor 16 further possesses a heater (not shown) for maintaining the catalyzed and the reference portions of the sensor at a constant, elevated temperature, which is sufficient to ensure that the catalytic oxidation process occurs, i.e., substantially complete oxidation of the remaining oxidizable species. Lastly, sensor the includes a means (not shown) for generating an output signal representative of the exothermic effect occurring as a result of the oxidation of the remaining oxidizable species in the exhaust gas portion. This means can simply comprise a means for measuring the temperatures of the first portion and second portion (unchanged after oxidation), both forming the output signal; a comparison of which would be representative of the amount of the heat released during the aforementioned oxidation; i.e., the exothermic effect.

In a second sensor embodiment, the catalytic differential calorimetric sensor 16 would be comprised of the identical first portion however the second or reference portion would also be catalytic. This sensor would be able to accurately measure the non-methane HC concentration even if small amounts of $CO+H_2$+alkanes remained unoxidized by the sensor catalyst. In this embodiment the reference portion of sensor would comprise an third oxidation catalyst comprising a catalyst-support material and a catalytically active precious metal capable of selectively oxidizing the combination of $CO+H_2$+alkene hydrocarbons. In the functioning of this second embodiment sensor, again the first portion would oxidize the remaining oxidizable species, which in this instance would not only include alkane and aromatic HC species, but also a small amount of $CO+H_2$+alkenes which remained un-oxidized; the reaction would be exothermic and again would raise the temperature of the first catalytic portion 22 above that of the reference portion 24. In this embodiment, however the reference portion would also be subject to a small exothermic reaction, the oxidation of the small amount of remaining $CO+H_2$+alkenes; the difference between the exotherms comprising the output signal of the sensor.

This second sensor embodiment would be possible only if the precious metal of each of the two, second and third, oxidation catalysts are maintained at the same temperature to achieve the substantial oxidation of the remaining oxidizable species and the $CO+H_2$+alkene hydrocarbons, respectively. In other words, since the respective oxidations occur at the same temperature the "selective" third oxidation catalyst can serve as the reference for comparison to the "remaining oxidizable species" second oxidation catalyst.

Figure 3:
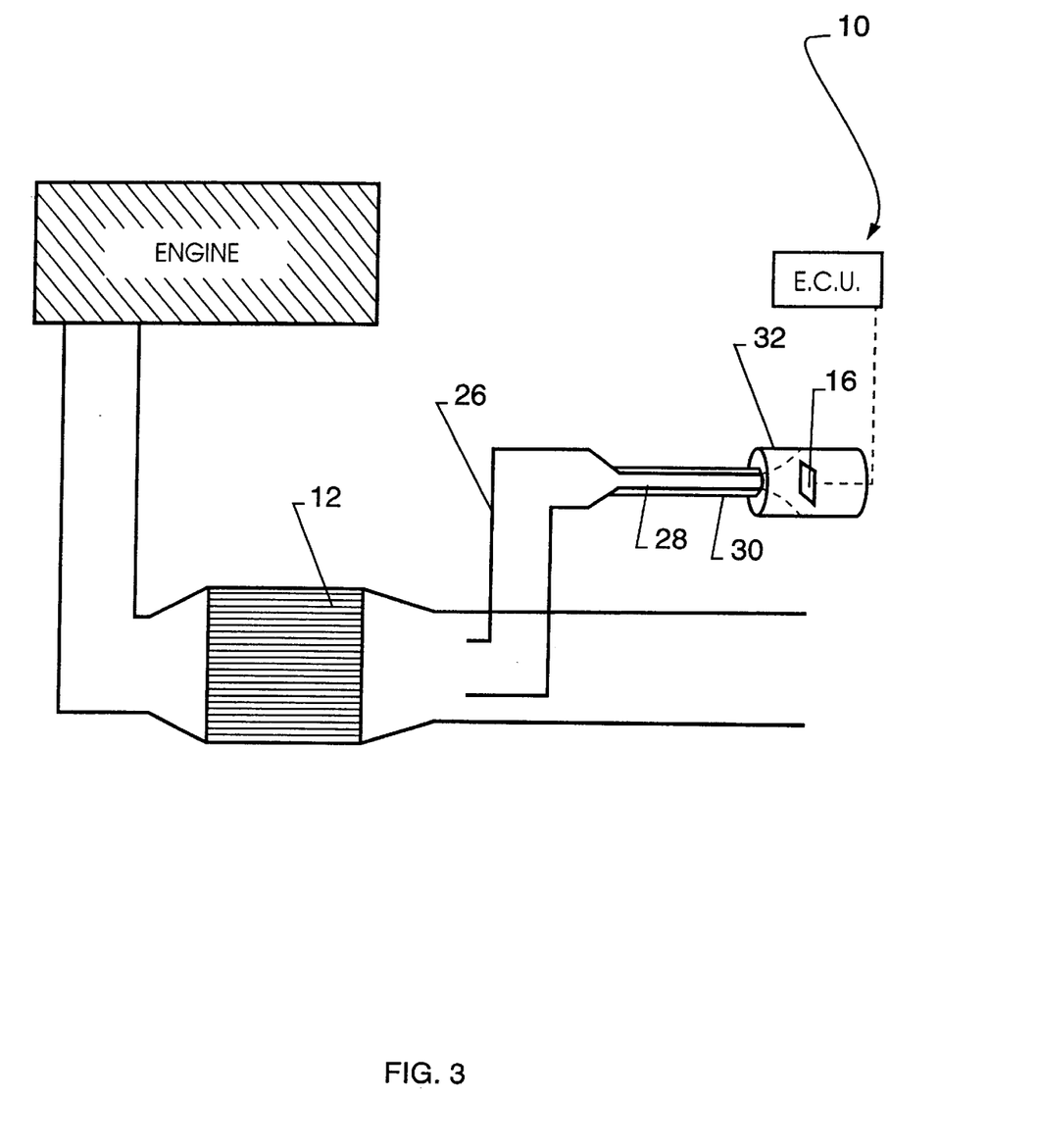
FIG. 3 is a schematic diagram of another embodiment of inventive system for measuring hydrocarbon concentration of an exhaust gas stream.

Referring now to FIG. 3, illustrated therein is another embodiment of the hydrocarbon measurement system 10, wherein the tubular housing 26, is not only located downstream of the main catalytic converter 12 it is remote or off-line from the main flow of the exhaust gas. In this embodiment the sensor catalyst 28 comprises a tubular body comprised of the catalyst-support material and upon which the precious metal is deposited; one benefit of this embodiment is that the tubular sensor catalyst 28 can be uniformly heated by a heater 30 that surrounds the sensor catalyst. The catalytic differential calorimetric sensor 16 is located within a separate downstream housing portion 32. Contrary to previous remote systems, this inventive system requires no complex valving means.

Suitable catalyst-support materials for the second oxidation catalyst include any high surface area material, preferably a ceramic material, including for example, silica, alumina, zirconia, and ceria. Since normal engines typically operate at a slightly rich A/F ratio, i.e., an A/F ratio around 14.6, more oxygen is required during these rich conditions so as to ensure that this second catalytic reaction occurs and thus this downstream sensor functions properly. Although excess oxygen can be supplied by providing an air supply line, or the like, to the exhaust gas, it is preferred that the excess oxygen be supplied through the use of a catalyst-support material that is comprised of oxygen storage material. In this case, the catalyst-support material is capable of storing and releasing oxygen depending upon the widely and rapidly varying oxygen concentration in the exhaust stream. Furthermore, use of oxygen storage materials as the catalyst-support material ensures that the catalytic calorimetric sensor functions properly (i.e., substantially complete oxidation of the remaining oxidizable species) even under fuel-rich conditions. This being said, it is preferred that the catalyst-support material be comprised of a ceria-containing material, more preferably ceria-zirconia solid solution.

Any catalytically active precious metal which is capable of oxidizing alkane and aromatic HC's, i.e., the remaining oxidizable species, present in the exhaust gas portion would be suitable for use in the second oxidation catalyst of the calorimetric sensor in the instant invention; suitable precious metals include rhodium, platinum, palladium, iridium, silver, gold, ruthenium, osmium, and mixtures thereof Preferably, the second oxidation catalyst for the catalytic calorimetric sensor 16 comprises platinum, palladium or a mixture thereof, supported by the aforementioned ceria-zirconia solid-solution catalyst-support material.

FIGS. 4 to 7 illustrate additional embodiments of the hydrocarbon measurement system according to the invention; the undesignated arrows indicating the direction of the flow of the exhaust gas. Like parts in each of the FIGS. 4 through 7, as described below, are identified with the same reference numerals used for the features described in FIG. 4.

Figure 4:
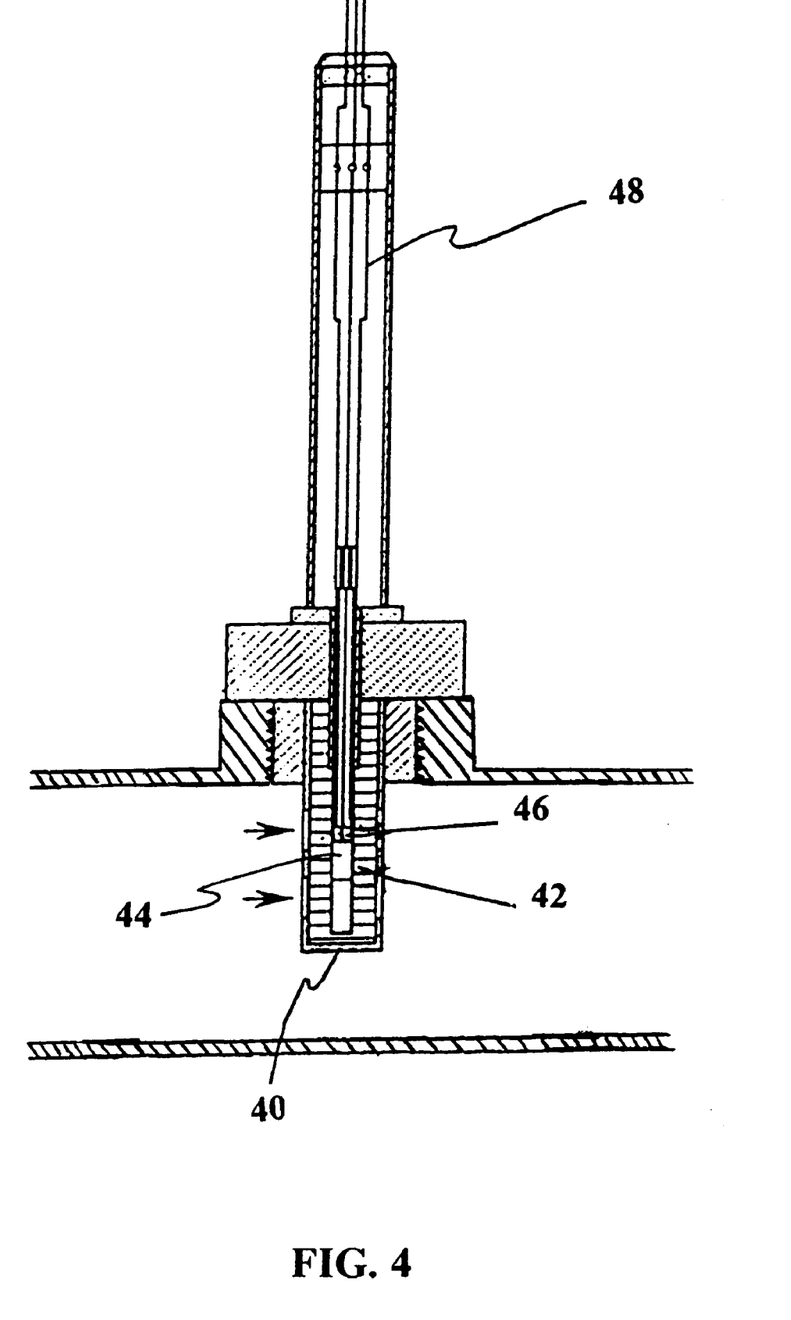
FIGS. 4 to 7 illustrate additional embodiments of inventive system for measuring hydrocarbon concentration of an exhaust gas.

Referring specifically now to FIG. 4, the hydrocarbon measurement system 10 is positioned such that at least a portion of the system is directly in contact with the main exhaust gas; i.e., an in-line measurement system. The hydrocarbon measurement system of FIG. 4 includes a perforated metal shroud 40 within which is located a honeycomb sensor catalyst 42, having channels that are parallel to the flow of the main exhaust gas. The honeycomb sensor catalyst 42, is coated with the aforementioned selective oxidation catalyst, has an open central region 44 into which is inserted a catalytic calorimetric sensor 46, as described above. The catalytic calorimetric sensor 46 is connected to a means 48 for measuring the output signal of the sensor to indicate the concentration of hydrocarbons in the exhaust gas. Briefly, the monitoring system functions in the following manner. The exhaust gas flows through the metal shroud 40 and into and through the sensor catalyst 42 that oxidizes all oxidizable species except for the aromatic and alkane hydrocarbons. The exhaust gas containing the remaining hydrocarbons then flows into contact with the sensor 46 whereupon the remaining aromatic and alkane hydrocarbons are catalyzed resulting in the sensor 46 producing an output signal representative of the exothermic effect occurring as a result of the oxidation of these remaining oxidizable hydrocarbon species. Simply stated, the exhaust gas flows through and is catalyzed by the sensor catalyst 42, contacts the calorimetric sensor 46 and then exits the sensor catalyst 42 flowing back into the main exhaust stream.

Figure 5:
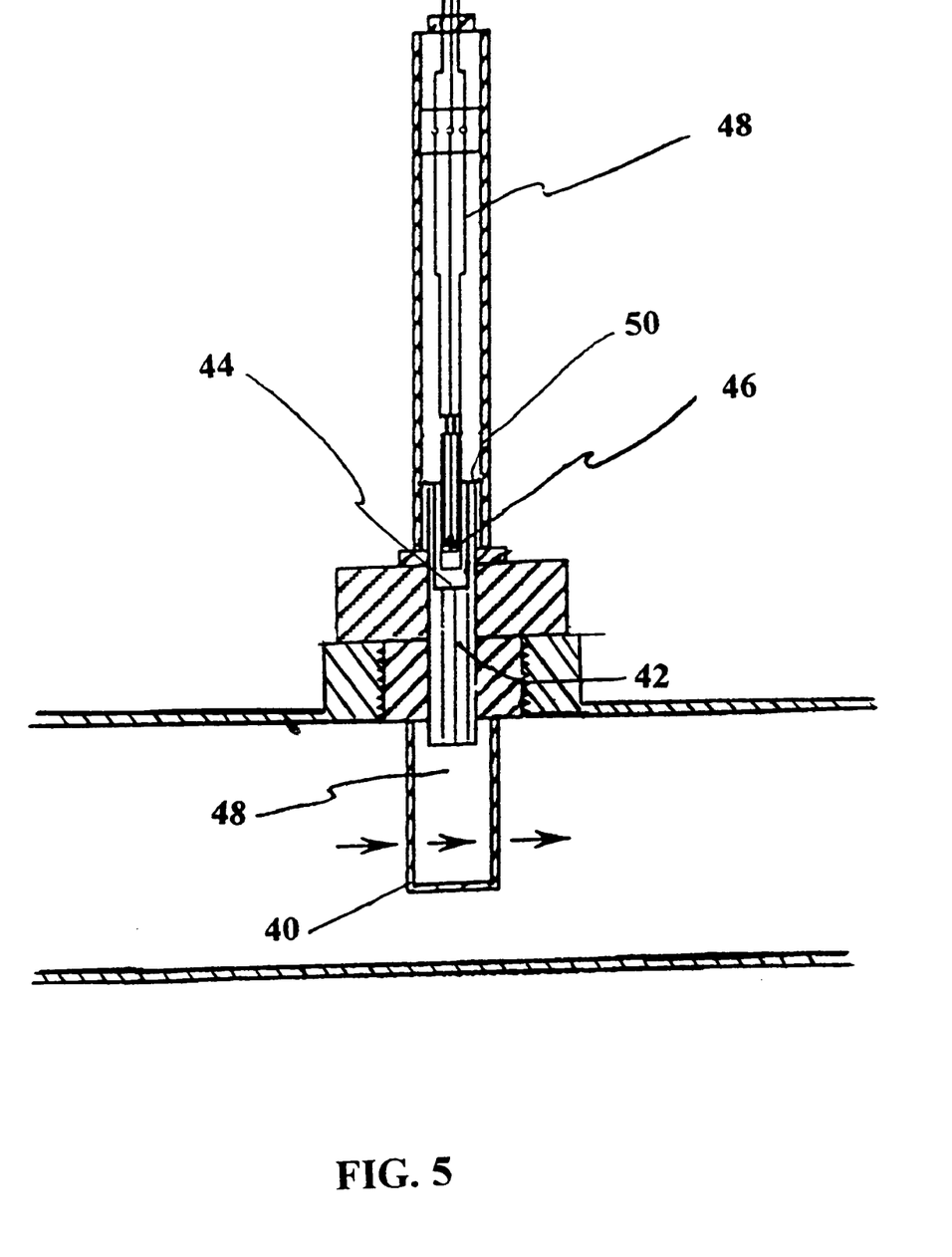

Referring specifically now to FIG. 5, the hydrocarbon measurement system again includes a perforated metal shroud 40, which is positioned to be within the flow of the main exhaust gas, however in this embodiment the metal shroud 40 has an open region 49. A honeycomb sensor catalyst 42, like in the embodiment of FIG. 4, again has an open central region 44 into which is inserted the calorimetric sensor 46. The honeycomb sensor catalyst 42 in this embodiment includes channels that are perpendicular to the flow of the exhaust gas and has a plugged downstream end 50. The measurement system of this embodiment functions in a similar manner to that of the system of FIG. 4, except that the exhaust gas flows through the metal shroud 40 and into, and then diffuses upwards through, the sensor catalyst 42 that oxidizes all oxidizable species except for the aromatic and alkane hydrocarbons. The exhaust gas containing the remaining hydrocarbons then diffuses into contact with the sensor 46 whereupon the remaining aromatic and alkane hydrocarbons are catalyzed resulting in the output signal representative of the exothermic effect occurring as a result of the oxidation of these remaining oxidizable species. In this embodiment, the exhaust gas is blocked from exiting the sensor catalyst and it diffuses into a channel having a lower concentration whereupon it diffuses back down the sensor catalyst 42 and into the open region 49 of the metal shroud 40 and then back into the main exhaust gas flow.

Figure 6:
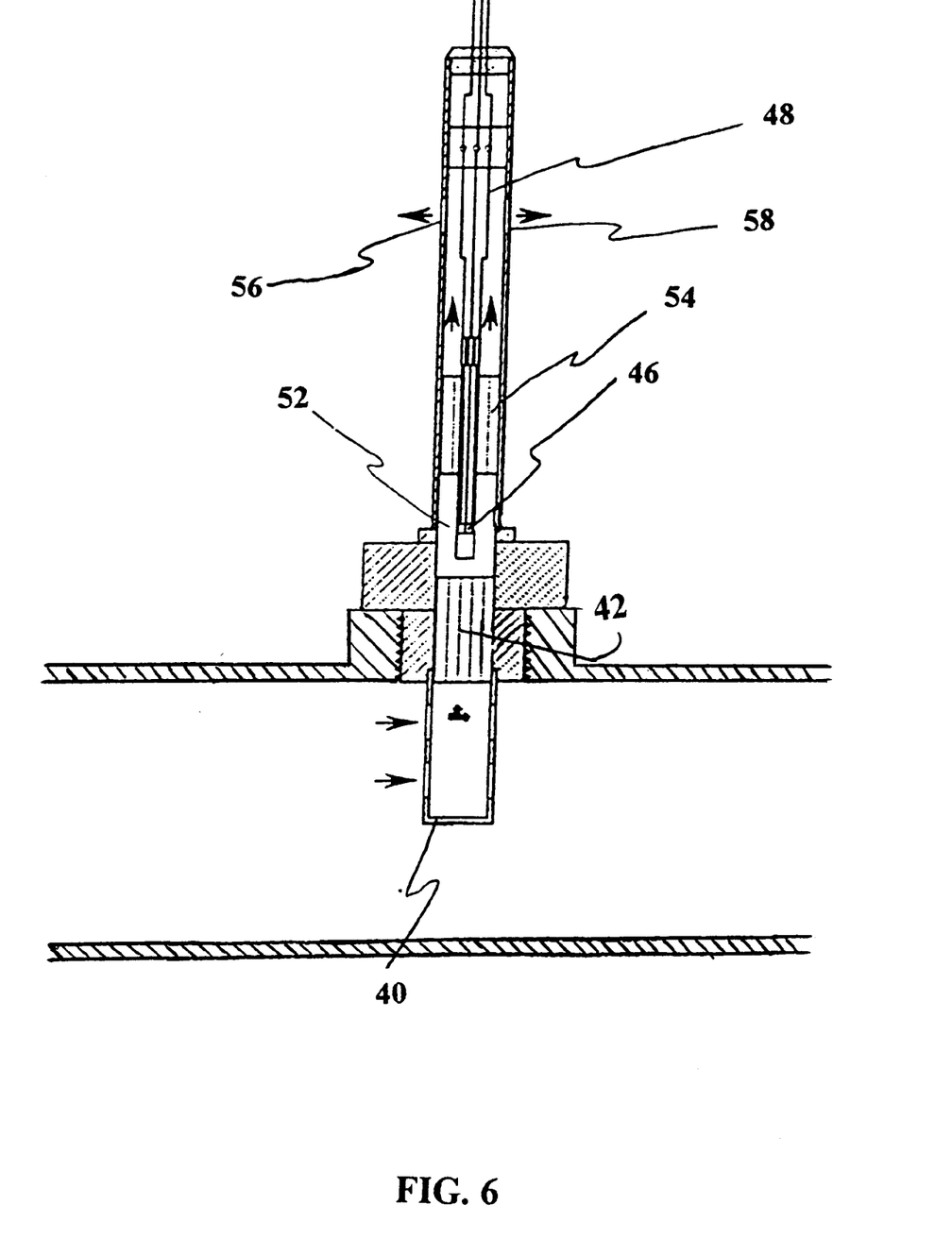

Referring now to FIG. 6, the catalyst monitoring system includes a perforated metal shroud 40, which is positioned to be within the flow of the exhaust gas, and again in this embodiment, the metal shroud 40 has an open region 49. In this embodiment the calorimetric sensor 46 is located downstream of the honeycomb sensor catalyst 42, in an open region 52. The channels of the honeycomb sensor catalyst 42 in this embodiment are again perpendicular to the flow of the main exhaust gas. This system further includes a uncatalyzed honeycomb support ring 54 having flow channels perpendicular to the main exhaust gas flow and two exit regions 56, 58 in the system housing. The measurement system of this embodiment functions in a similar manner to that of the system of FIG. 5 except that the exhaust gas flow is not blocked from flowing through the sensor catalyst 42. As such, the catalyzed exhaust gas flows through the sensor catalyst and into the open region 52 and contacts the calorimetric sensor and then flows through the honeycomb support ring 54 and then through the exit regions 56, 58 and into the atmosphere.

Figure 7:
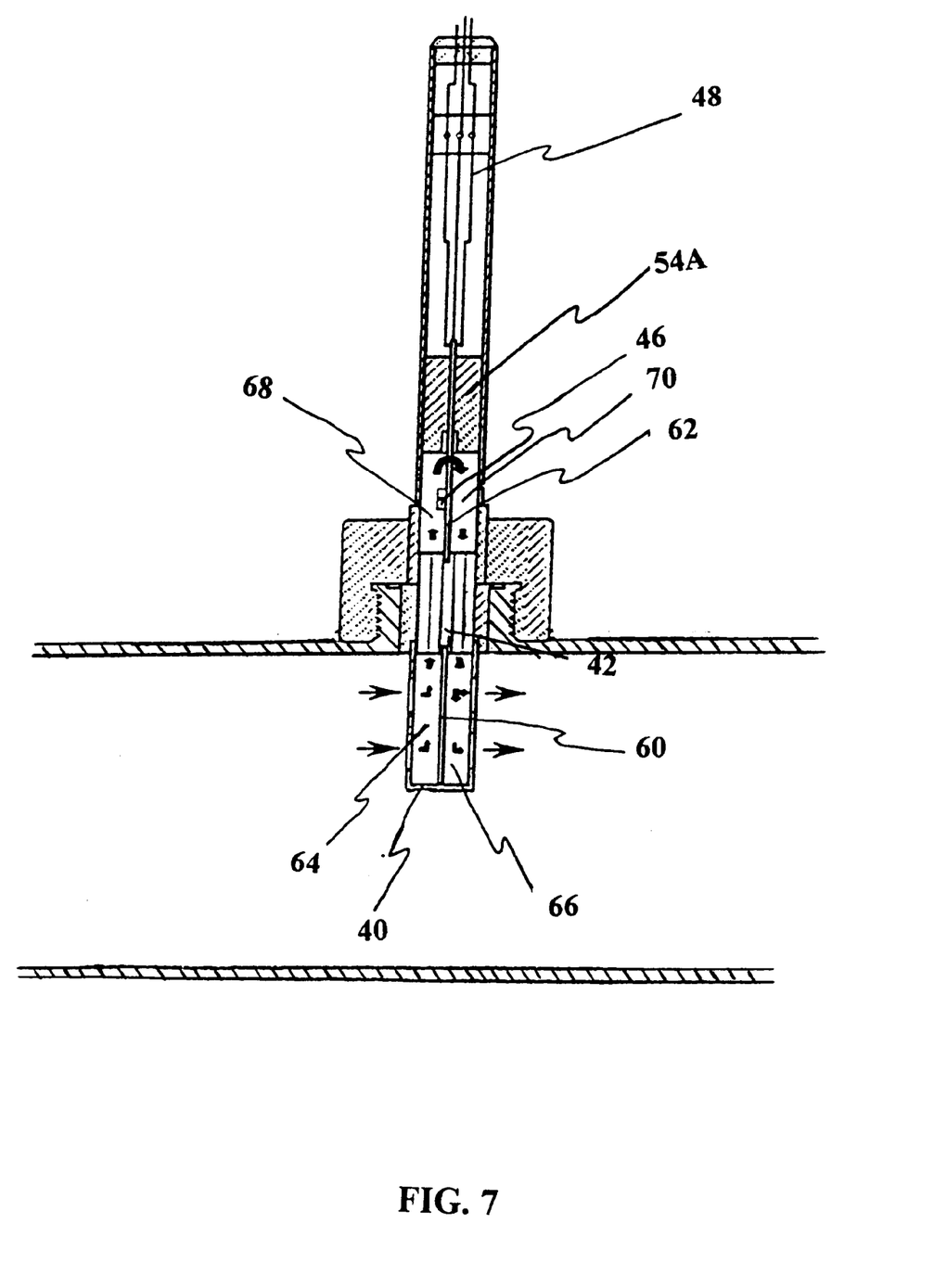

Referring now to FIG. 7, the catalyst monitoring system includes a perforated metal shroud 40, which is positioned to be within the flow of the exhaust gas, and again in this embodiment the metal shroud 40 has an open region 49. In this embodiment, however, both the metal shroud open region 49 and the downstream open region 52 include a metal divider 60, 62, respectively, which divides each of the metal shroud and downstream open regions into two separate portions, an entrance and an exit portion, 64,66 and 68,70 respectively. The downstream metal divider 62 has an open portion 72 that allows communication between the divided entrance 68 and exit 70 regions. As in the FIG. 7 embodiment, the calorimetric sensor is located downstream of the honeycomb sensor catalyst 40 and in the entrance portion 68 of the open region. The honeycomb sensor catalyst in this embodiment includes channels that are perpendicular to the flow of the exhaust gas. This system further includes support ring 54A that does not allow any exhaust to flow through. The measurement system of this embodiment functions in a similar manner to that of the system of FIG. 6 except that the exhaust gas flow is blocked from flowing through the support 54A and as such the catalyzed exhaust gas is caused to flow from the entrance region 68 through the open portion 72 and into the exit region 70 and back into the sensor catalyst 42 and further into the metal shroud exit region 66 and then into the main exhaust gas flow.

Figure 8:
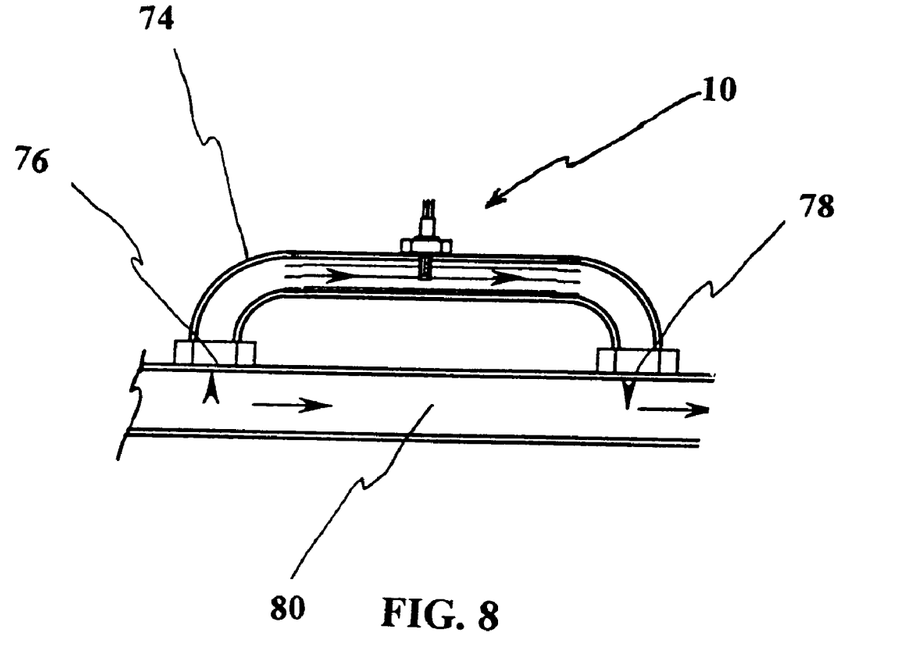
FIG. 8 is a schematic illustration of an additional positioning of the inventive systems for measuring hydrocarbon concentration of FIGS. 4 to 7.

Referring now to FIG. 8, illustrated therein is an alternative off-line positioning of the hydrocarbon monitoring systems illustrated in FIGS. 4–7. Specifically, the hydrocarbon measurement system 10 is located in a bypass channel 74 that has its entrance 76 and exit 78 connected to the housing 80 of the main exhaust flow.

In a preferred embodiment the sensor catalyst utilized in the embodiments of FIGS. 4–7 is an oxidation catalyst that comprises a honeycomb cordierite substrate upon which is provided, a dual layer of high surface area catalyst support materials, specifically a washcoat layer comprising a mixture of $SiO_2$ $_{and\ K-Al2}O_3$. The highly dispersed Rh-cluster deposits are located on this dual-material mixture washcoat layer. The catalytic calorimetric sensor preferably comprises a divided sensor device with the second oxidation catalyst portion comprising a $CeO_2$—$ZrO_2$ catalyst-support material having a catalytically active precious metal layer, comprising Pt, formed thereon. The second or reference portion of this divided sensor is an oxidation catalyst, the third oxidation catalyst comprising a high surface area $SiO_2$ catalyst-support material having a catalytically active precious metal layer, comprising highly dispersed Rh, formed thereon.

As described above, the above-described sensor design employs some means for measuring the extent of the exotherm; i.e., a means for measuring the increase in the temperature of the oxidizing portion, as well the reference temperature of the non-oxidizing/reference portion which remains unchanged after the oxidation in one embodiment and increases slightly in another.

In sum, the temperature of the divided sensor portions, catalytic and non-catalytic is measured so as to calculate the following:

the difference between the temperatures of the catalyzed (increased as result of catalytic oxidation) and the reference portions (reference temperature which remains unchanged throughout the oxidation in one embodiment and which slightly increases in another) of the sensor which is a measure of the exothermic effect, of the oxidation of all the remaining oxidizable species in a downstream portion of the exhaust gas. $-T=$ [aromatic+alkane HC].

The temperature measuring device may be well known devices such as thermistors, thermopiles or thermocouples which are incorporated within the aforementioned substrate and which are capable of detecting the temperature of the reference portion and the temperature rise of the catalyzed portion, occurring as a result of the oxidation reactions described above; the difference being the result of the oxidation exotherm. If thermocouples or thermopiles are used they would require a separate heater; e.g., a heating coil which would maintain the substrate at a temperature such that the oxidation catalyst would be maintained at the aforementioned temperature sufficient to achieve substantially complete oxidation.

In another embodiment a resistance-temperature detector (RTD) would be incorporated into each of the catalytic and reference portions of the substrate of each respective sensor device; the RTD would perform the dual functions of maintaining the catalyst portion at a temperature sufficient to effect substantially complete oxidation and the measurement of the temperature increase occurring after oxidation. Specifically, each of the RTDs would be operated by heating the substrate to a set temperature by passing a current to each and thereafter measuring the difference in required current necessary to maintain the set temperature of the oxidation and reference RTD; this difference would be a measure of the oxidation exotherm occurring as result of whichever oxidation reaction is occurring.

Regardless of the means used to measure the respective temperatures, these measured temperatures are converted to an electrically measurable quantity (voltage, resistance or current etc.) by the temperature measuring means and thereafter analyzed to generate the aromatic and alkane hydrocarbon concentration and thus the total hydrocarbon concentration. It is contemplated that a microprocessor based electronic control unit (ECU) can be used as the aforementioned means to analyze the measurable temperature outputs to generate the output signal of the catalytic differential calorimetric sensor. The ECU would thereafter analyze the exotherm to indicate the aromatic and alkane concentration and thereafter the total concentration of unburned hydrocarbons in the downstream exhaust gas.

Method

The present invention is also directed at a method of directly measuring the hydrocarbon concentration of the exhaust gases in an exhaust gas stream. Generally, the method involves the steps of selectively oxidizing a portion of the exhaust gas and thereafter contacting that oxidized portion with a sensor that measures the hydrocarbons remaining in the exhaust gas. The output signal of the sensor is then analyzed to determine the hydrocarbon concentration of the exhaust gas.

It should be noted that the portions can be measured in a whatever manner is most practical; i.e., either in-line or off-line, assuming that the portion which is contacted with the sensor has already been subjected to catalytic oxidation. It is only important that the portion measured comprises substantially the same exhaust gas composition as that of the actual exhaust gas composition.

Having described in a general sense a method for directly measuring the hydrocarbon concentration, the following is a more detailed description of the steps of the method. The step of selectively oxidizing an exhaust gas portion involves causing the exhaust gas portion to come into contact with a sensor catalyst and selectively oxidizing the $CO+H_2+$alkene species present in the exhaust gas portion. The oxidized exhaust gas portion is thereafter caused to come into contact with a catalytic differential calorimetric sensor and catalytically oxidizing the remaining oxidizable species present in the exhaust gas portion; the alkane and aromatic hydrocarbon species. The resultant oxidation reaction causes a temperature increase in the catalyzed portion of the sensor $-T=$[alkane+aromatic HCs] which is thereafter used for producing a signal representative of this exothermic effect.

Lastly the output signals, i.e., the exotherm, is analyzed to generate the sum of the alkane and aromatic hydrocarbon concentration in the exhaust gas. In turn, this direct and selective measurement of aromatic and alkane HC concentration, in the presence of other oxidizable species such as CO and $H_2$ can thereafter be analyzed to generate the total non-methane HC concentration; assuming that there is a direct correlation between the aromatic and alkane hydrocarbon concentration and the total HC concentration (see description below).

Exhaust gas, for instance, contains greater than 200 species of HCs that can be divided into the alkene, alkane and aromatic species or families. Table I details a representative example of an engine exhaust data from a 1991 Buick Park Avenue automobile. The test was conducted in accordance with the FTP procedure for measuring accumulated engine exhaust emissions. Reported in Table I for the exhaust system test conducted are the following hydrocarbon emissions for the entire test cycle, reported in grams per mile: (1) the total non-methane hydrocarbons (NMHC); (2) the total alkene hydrocarbons; (3) the aromatic hydrocarbons; and, (4) the alkane hydrocarbons. Also reported are the percentage (%) of the total NMHC, which each of the hydrocarbon species alkene, aromatic, alkane and aromatic+alkane comprised. The two stages of the Bag I portion of the test comprised an initial or cold-start test stage (0–60 seconds) and an intermediate stage (60–505 seconds); a Bag II stage lasting from >505–1372 seconds follows.

TABLE I

| | Initial Bag I Stage (cold-start: 0–60 secs.) | Intermediate Bag I Stage (60–505 secs) | Bag II Stage (505–1372 secs.) |
| --- | --- | --- | --- |
| Total NMHC (mg) | 1655 | 178 | 80 |
| Alkenes (mg) | 201 | 20 | 11 |
| Aromatics (mg) | 453 | 57 | 19 |
| Alkanes (mg) | 1001 | 101 | 50 |
| Alkane/NMHC (%) | 12 | 11.2 | 13.7 |
| Aromatic/NMHC (%) | 27.4 | 32 | 23.8 |
| Alkane/NMHC (%) | 60.6 | 56.8 | 62.5 |
| (Aromatic + Alkanes)/NMHC (%) | 88 | 88.8 | 86.3 |

As is apparent from a study of the data set forth in Table I, car exhaust, during a typical FTP cycle, exhibits a composition in which the alkane and aromatic hydrocarbons account for greater than approximately 85% of the total HCs. Therefore, a selective HC sensor that detects only aromatics and alkanes with no interference from carbon monoxide or $H_2$ oxidation, is a practical device for measuring the total hydrocarbon concentration as there is a direct correlation between the combined aromatics and alkane concentration and the total HC concentration.

In the embodiment described above, when the exhaust gas portion is measured downstream of the catalytic converter, and therefore the hydrocarbon concentration of the exhaust gas is determined downstream of the catalytic converter, this measuring of the hydrocarbon concentration is, in actuality, a measure of how well the catalytic converter is functioning; i.e., a system for monitoring the performance of the catalytic converter efficiency. In other words, the concentration of the aromatic and alkane hydrocarbon present in the oxidized exhaust gas portion, downstream of the catalytic converter, directly correlates to the total HC concentration, and thus how well the catalytic converter is functioning. As such, this method is a practical and accurate method for monitoring the hydrocarbon catalytic converter efficiency as required by OBD II.

EXAMPLES

The following examples illustrate the functionality of both the "selective" sensor catalyst and the divided sensor device. In both cases the experimental device comprises of a pair of thermocouples as follows: (1) one uncatalyzed thermocouple, upon which is deposited a ceramic catalyst-support material which will generate a reference voltage/temperature; and, (2) one catalyzed thermocouple, upon which is deposited a the ceramic catalyst-support material and the precious metal catalyst material, and upon which oxidation and a resultant temperature increase will occur.

A "selective" sensor catalyst, i.e. one which only oxidizes carbon monoxide, alkene hydrocarbons and $H_2$, was prepared and tested in the following manner:

Formation of the catalyst-support material/catalytically active precious metal mixture first involved forming 3 Omg of a rhodium chloride solution (10%, by weight, Rh) by adding rhodium chloride powder, as supplied by the Aldrich Chemical Company Inc., Milwaukee, Wis., to the necessary amount of water. This rhodium chloride solution was dissolved into a sufficient amount of ammonia hydroxide solution to form 30 mls of a second solution having a pH of 12. 10 g of a fumed silica material, manufactured and sold by the Degussa Corporation, Ridgefield Park, N.J., as AEROSIL 130, was thereafter impregnated with 30 mls of the rhodium solution and mixed sufficiently to form a silica slurry, which was thereafter dried in an oven for one day at a temperature of 130° C. The dried powder was first, calcined and reduced for one hour at a temperature of 300° C. in an atmosphere consisting of 6%$H_2$/$N_2$ and thereafter calcined in a flowing air atmosphere for 4 hours at a temperature of 500° C.

An aqueous slurry comprised of the above calcined powder was formed and thereafter dip-coated as a 1 mm$^3$ bead onto the tip of a type-K thermocouple; i.e., a catalyzed portion. The second oxidation-catalyst-free portion also comprised a type K thermocouple that was dip-coated to form a 1 mm$^3$ bead, however the bead consisted of a high surface area catalytically-inactive $SiO_2$ material. Both coated thermocouples were dried as above.

The "selective" sensor catalyst was tested for selective oxidation effect by placement in a tubular flow-through reactor and by connecting the thermocouple to a multi-pin feedthrough. Various reaction gas combinations were introduced into the reactor, via mass flow controllers, at a constant flow rate of 7508 cc/min. The furnace was heated to, and maintained throughout the testing, at a temperature of 360° C., resulting in a thermocouple temperature of 270° C. The base or initial reaction gas to which various test gases (see Table II) were added consisted of 14% $CO_2$, 1% $O_2$, with the balance being made up of $N_2$.

Various concentrations of CO, propylene (alkene HC), isopentane (alkane HC), and toluene (aromatic HC) were introduced into the reactor with $N_2$ flow again adjusted to maintain constant total flow rate. Table II reports the various concentrations of these gases, in parts per million (ppm), and the reaction rate of the gases on the catalyst surface as monitored by the temperature difference between the catalyzed and un-catalyzed thermocouples (−T).

TABLE II

| Test No | Test Gas Concentration | −T (° C.) |
|---|---|---|
| 1 | 10,000 ppm CO | 35 |
| 2 | 1000 ppm $C_3H_6$ | 5 |
| 3 | 500 ppm toluene | 0 |
| 4 | 1000 ppm isopentane | 0 |

An examination of Table II reveals the following: (1) test sample 1, the presence of 10,000 ppm CO in the exhaust, produced a temperature rise, or −T, of 35° C. indicating significant amount of CO being oxidized; (2) test sample 2, the presence of 1000 ppm of the alkene, propylene, in the gas stream, produced a temperature rise of 5° C., indicating moderate activity of the catalyst for propylene; and, (3) test samples 3 and 4, the presence of 500 ppm of an aromatic hydrocarbon, toluene, and 1000 ppm of an alkane, isopentane, respectively, produce no temperature change indicating the catalyst has no activity for isopentane and toluene.

Based on the above observations it is clear that this catalyst-support material/catalytically active precious metal mixture would be suitable to use in the instant invention as the sensor oxidation catalyst which selectively oxidizes CO and alkenes, but is inactive for aromatic and alkane hydrocarbons.

The first or "remaining-oxidation species" sensor device was prepared and tested in the following manner:

A ceria stabilized zirconia/platinum powder mixture was prepared comprising a mixture consisting of 59.31 grams of cerium nitrate and 107.6 grams of zirconyl nitrate hydrate, both supplied by the Aldrich Chemical Company, Inc., Milwaukee, Wis. The mixture was dissolved in water to produce a 500 ml, 4N solution which was thereafter added dropwise to a 500 ml ammonium hydroxide aqueous solution. Following precipitation of cerium and zirconium hydroxides, the precipitate was thoroughly washed with $H_2O$ and thereafter dried overnight in an oven at 130° C. and thereafter calcined for four hours in stagnant air at a temperature of 500° C.

Ten grams of the calcined ceria stabilized zirconia was "incipient wetness" impregnated with 3.0 g of hexachloroplatininc acid solution (Aldrich Chemical Company, Inc.) having a platinum content of about 10% by weight. The impregnated powder was again dried overnight in an oven at a temperature of 130° C. and thereafter calcined at 500° C. for four hours thereby forming a ceria stabilized zirconia material having 3% by weight Pt dispersed therein.

The actual "remaining oxidation species" sensor was thereafter formed in the following manner:

An aqueous slurry comprised of the above calcined powder was formed and thereafter dip-coated as a 1 mm$^3$ bead onto the tip of a type-K thermocouple; i.e., the first catalyzed portion. The second oxidation-catalyst-free portion also comprised a type K thermocouple which was dip-coated to form a 1 mm$^3$ bead, however the bead consisted of a catalytically inactive $Al_2O_3$ material; the second reference portion. Specifically, the catalytically inactive $Al_2O_3$ material comprised an aqueous slurry of Boehmite alumina, 20% by weight alumina, as manufactured by the PQ Corporation, Ft. Washington, Pa. Both coated thermocouples were thereafter rapidly dried by heating them with a heat gun exhibiting a temperature of approximately 350° C.

The thermocouple pair forming the "remaining oxidation species" sensor was tested for oxidation response by placement in a tubular flow-through reactor by connecting them to a multi-pin feedthrough. Various reaction gas combinations were introduced into the reactor, via mass flow controllers, at a constant flow rate of 7508 cc/min. The furnace was heated to, and maintained throughout the testing, at a temperature of 440° C., resulting in a thermocouple temperature of 380° C. The base or initial reaction gas to which the various test gases (see below) were added, as before, consisted of 14% $CO_2$, 1% $O_2$, with the balance being made up of $N_2$ FIG. 9 reports the temperature differential which resulted between the two thermocouples of the sensor as a function of adding increasing amounts of isopentane ($C_5H_{12}$) to the initial gas; in each case the amount of $N_2$ was modified in order to maintain the constant total flow rate of 7508 cc/min. The data shows a strong linear dependence of the −T signal as the concentration of isopentane in the reaction gas increases from zero to 1000 ppm.

Figure 9:
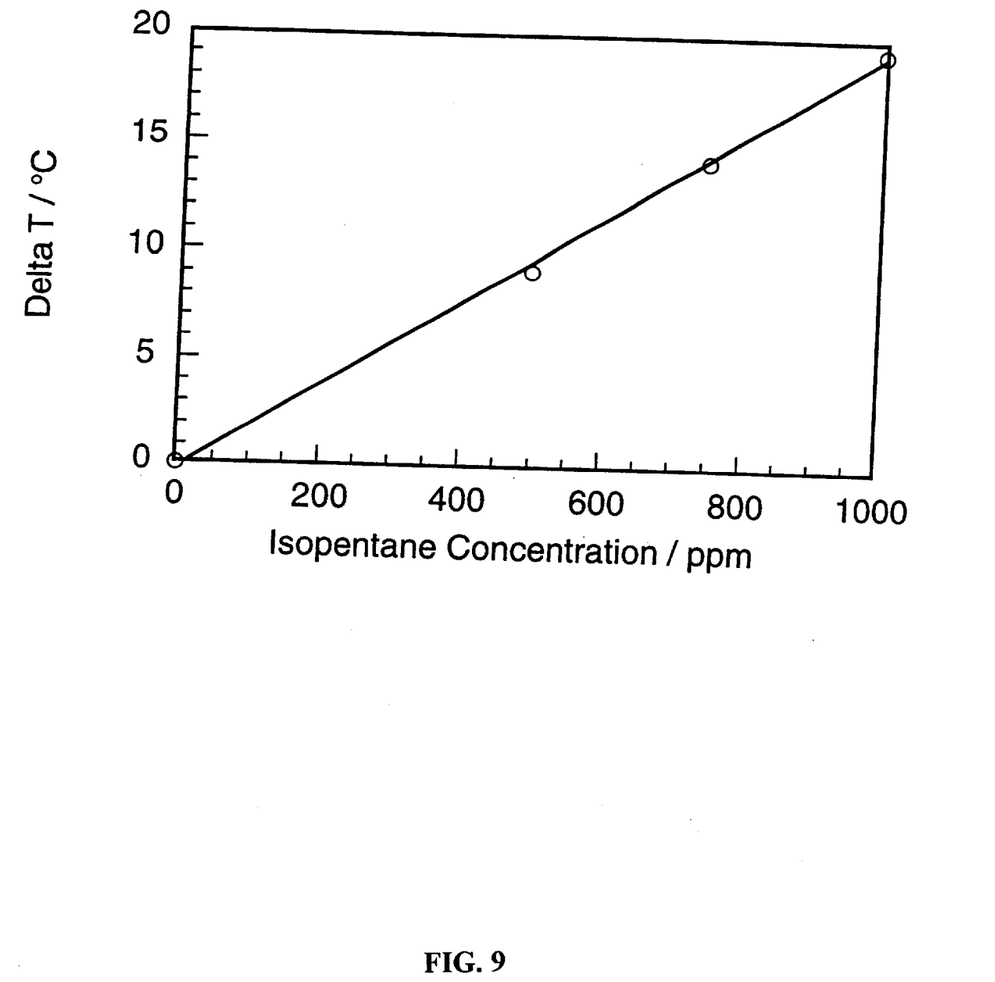
FIG. 9 is a graphical illustration of the temperature change (−T) between a catalytic and reference thermocouple of a divided sensor device Example as a function of the isopentane (2-methyl-butane) concentration.

The linear dependence of the −T signal as the concentration of gas increases, which is shown for the above FIG/test gas, demonstrates the ability to readily calibrate a −T output signal representative of the oxidation exotherm effect discussed above. Furthermore, the above data and FIG support the proposition that this catalytic differential calorimetric sensor will function effectively as the "remaining species oxidation" sensor as it readily oxidizes the alkane hydrocarbon, isopentane, it is assumed therefore that the aromatics will be oxidized as well.

Although the now preferred embodiments of the invention have been set forth, it will be apparent to those skilled in the art that various changes and modifications may be made thereto without departing from the spirit and scope of the invention as set forth in the following claims.

We claim:

1. A system for measuring the hydrocarbon concentration of a gas sample, comprising:

a sensor catalyst having an oxidation catalyst capable of selectively oxidizing the combination of $CO+H_2+$ alkene hydrocarbons species in the gas sample, the sensor catalyst comprising an oxidation catalyst having a high surface area catalyst-support material and a precious metal layer comprising an amount of highly dispersed rhodium cluster deposits on the surface of a high surface area catalyst-support material, the rhodium cluster deposits comprising a single rhodium atom or a cluster of at least two rhodium atoms, the deposits having a diameter of less than about 5 nm and covering no greater than about 10% of the surface area of the catalyst-support material;

a catalytic differential calorimetric sensor, capable of producing a output signal representative of the exothermic effect of the remaining aromatic and alkane hydrocarbons species in the gas sample; and, a heater for maintaining each of the sensor catalyst and the catalytic calorimetric sensor at a temperature sufficient to effect substantially complete oxidation of the $CO+H_2+$alkene hydrocarbon and aromatic and alkane hydrocarbon species, respectively;

a means for analyzing the output signal representative of the concentration of unburned aromatic and alkane hydrocarbons in the exhaust gas to determine concentration of the total non-methane hydrocarbon species.

2. The system of claim 1 wherein the catalyst-support material is comprised of a material selected from the group consisting of alumina, zirconia, silica, ceria and mixtures thereof.

3. The system of claim 1 wherein the oxidation catalyst of the sensor catalyst is comprised of a dual layer washcoat layer comprising a mixture of $SiO_2$ and $K-Al_2O_3$ and a precious metal layer comprising Rh.

4. The system of claim 1 wherein the sensor catalyst and the differential catalytic calorimetric sensor are located within a tubular housing which is located in an internal combustion engine exhaust stream downstream of a main catalytic converter.

5. The system of claim 1 wherein the catalytic differential calorimetric sensor comprises a substrate comprising a first catalytic portion having a second oxidation catalyst capable of oxidizing the remaining alkane and aromatic hydrocarbon species in the gas sample and an adjacent second reference portion.

6. The system of claim 5 wherein the sensor includes a means for measuring the temperature the catalyzed portion and the second reference portion.

7. The system of claim 6 wherein the means of measuring the temperature is selected from the group consisting of thermocouples, thermistors and resistance temperature devices.

8. The system of claim 6 wherein both the heater and the means for measuring the temperature comprises a resistance temperature device.

9. The system of claim 5 wherein the adjacent second reference portion comprises a third oxidation catalyst comprising a catalytic-support material and a precious metal material capable of selectively oxidizing the combination of $CO+H_2+$alkene hydrocarbons.

10. The system of claim 9 wherein the second oxidation catalyst is comprised of a high surface area catalyst-support material and a precious metal material.

11. The system of claim 10 wherein the precious metal of the second oxidation catalyst is selected from the group consisting of rhodium, platinum, palladium, iridium, silver, gold, ruthenium, osmium, and mixtures thereof.

12. The system of claim 10 wherein the second oxidation catalyst is comprised of a ceria/zirconia solid solution catalyst-support material and a precious metal comprised of platinum.

* * * * *